United States Patent
Dwivedi et al.

(10) Patent No.: US 10,414,741 B2
(45) Date of Patent: Sep. 17, 2019

(54) AMORPHOUS VORTIOXETINE AND SALTS THEREOF

(71) Applicant: CADILA HEALTHCARE LIMITED, Ahmedabad, Gujarat (IN)

(72) Inventors: Shri Prakash Dhar Dwivedi, Gujarat (IN); Kumar Kamlesh Singh, Gujarat (IN); Jitendra Maganbhai Gajera, Gujarat (IN); Dinesh Kumar Raikwar, Gujarat (IN); Brij Khera, Gujarat (IN)

(73) Assignee: CADILA HEALTHCARE LIMITED, Ahmedabad, Gujarat (IN)

( * ) Notice: Subject to any disclaimer, the term of this patent is extended or adjusted under 35 U.S.C. 154(b) by 0 days.

(21) Appl. No.: 14/916,075

(22) PCT Filed: Sep. 30, 2014

(86) PCT No.: PCT/IN2014/000633
§ 371 (c)(1),
(2) Date: Mar. 2, 2016

(87) PCT Pub. No.: WO2015/044963
PCT Pub. Date: Apr. 2, 2015

(65) Prior Publication Data
US 2016/0214949 A1  Jul. 28, 2016

(30) Foreign Application Priority Data

Sep. 30, 2013 (IN) .......................... 3121/MUM/2013

(51) Int. Cl.
*C07D 295/096* (2006.01)
(52) U.S. Cl.
CPC ................. *C07D 295/096* (2013.01)
(58) Field of Classification Search
None
See application file for complete search history.

(56) References Cited

U.S. PATENT DOCUMENTS

| 7,144,884 B2 | 12/2006 | Ruhland et al. |
| 2010/0297240 A1 * | 11/2010 | Bang-Andersen ............ C07D 295/096 424/489 |
| 2012/0004409 A1 | 1/2012 | Nicolajsen et al. |

FOREIGN PATENT DOCUMENTS

| WO | 2003/029232 A1 | 4/2003 | |
| WO | 2007/144005 A1 | 12/2007 | |
| WO | 2010/094285 A1 | 8/2010 | |
| WO | 2013/102573 A1 | 7/2013 | |
| WO | WO-2014044721 A1 * | 3/2014 | ......... C07D 295/096 |
| WO | 2014/177491 A1 | 11/2014 | |
| WO | WO 2016062860 A1 * | 4/2016 | ........... A61K 9/2031 |

OTHER PUBLICATIONS http://www.americanpharmaceuticalreview.com/Featured-Articles/119521-Developing-Amorphous-Pharmaceuticals-Opportunity-and-Necessity/ referenced on Jun. 26, 2017.*
International Search Report issued in PCT/IN2014/000633, dated Mar. 30, 2015 (3 pages).
USFDA Clinical Pharmacology and BioPharmaceutics Review(s); Center for Drug Evaluation and Research (121 pgs).
USFDA Clinical Review DOP Oct. 30, 2013 (1 pg).

* cited by examiner

*Primary Examiner* — Jessica Worsham
(74) *Attorney, Agent, or Firm* — Nixon & Vanderhye P.C.

(57) ABSTRACT

The present invention relates to an amorphous vortioxetine and salts thereof. In particular, the invention relates to a process for the preparation of an amorphous vortioxetine hydrobromide. Further, the invention also relates to a process for preparation of amorphous vortioxetine free base. The invention also relates to pharmaceutical compositions comprising an amorphous vortioxetine or hydrobromide salt thereof for oral administration for treatment of major depressive disorder (MDD) and generalized anxiety disorder (GAD).

13 Claims, 3 Drawing Sheets

AMORPHOUS VORTIOXETINE AND SALTS THEREOF

Figure 1:
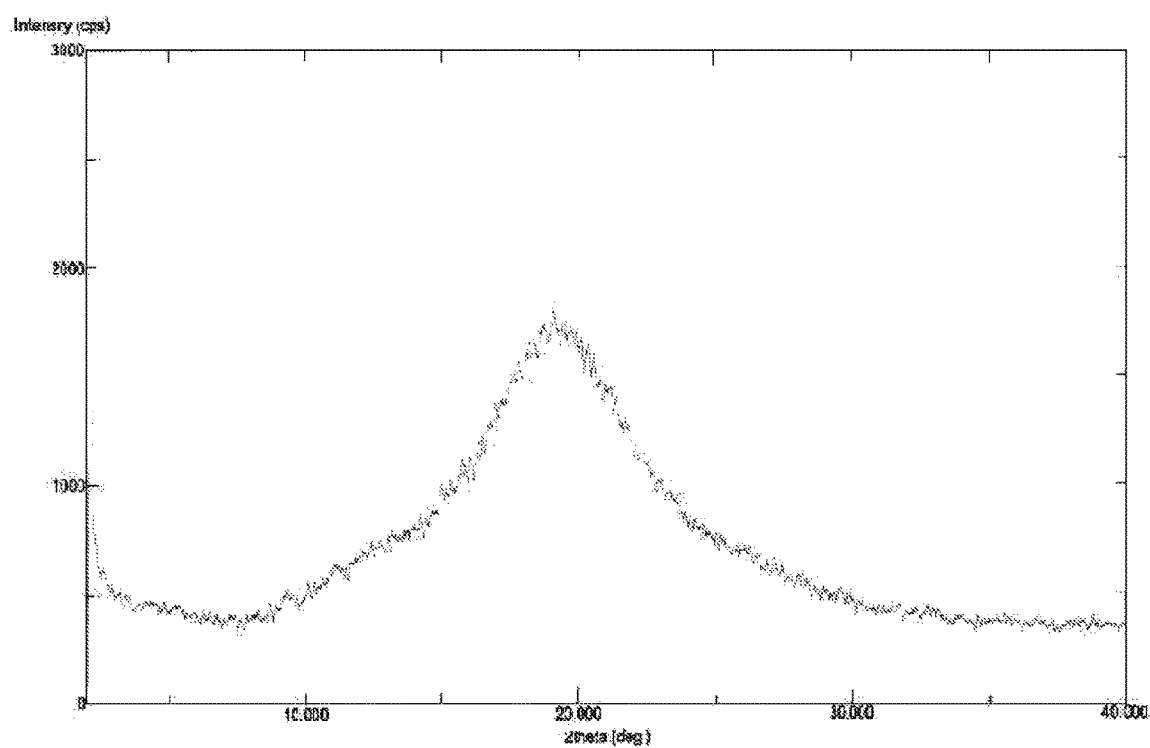

This application is a U.S. National Phase of International Application No. PCT/IN2014/0006333 filed Sep. 30, 2014, which claims priority to IN 3121/MUM/2013 filed Sep. 30, 2013, the entire contents of each of which are hereby incorporated by reference.

FIELD OF THE INVENTION

The field of the invention relates to an amorphous vortioxetine and salts thereof. In particular, the invention relates to a process for the preparation of an amorphous vortioxetine hydrobromide. Further, the invention also relates to a process for preparation of amorphous vortioxetine free base. The invention also relates to pharmaceutical compositions comprising an amorphous vortioxetine or hydrobromide salt thereof for oral administration for treatment of major depressive disorder (MDD) and generalized anxiety disorder (GAD).

BACKGROUND OF THE INVENTION

The following discussion of the prior art was intended to present the invention in an appropriate technical context and allow its significance to be properly appreciated. Unless clearly indicated to the contrary, however, reference to any prior art in this specification should be construed as an admission that such art was widely known or forms part of common general knowledge in the field.

"Vortioxetine" (also known as Lu AA21004) is chemically known as 1-{2-[(2,4-dimethylphenyl)sulfanyl] phenyl}piperazine of Formula (I), and as hydrobromide salt.

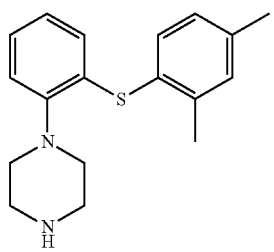

(I)

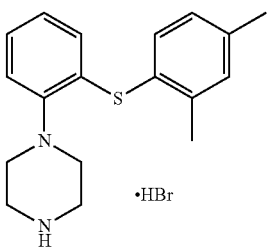

(II)

Vortioxetine is currently under development by Lundbeck and Takeda for the treatment of major depressive disorder (MDD) and generalized anxiety disorder (GAD). Regulatory approval for the treatment of MDD has been filed Europe and USA. It is a serotonine modulator and stimulator.

Vortioxetin was first disclosed specifically in U.S. Pat. No. 7,144,884 B2 and six alternative approaches to prepare compounds analogous to vortioxetine were provided.

U. S. PG-Pub. No. 2010/297240 A1 (The US '240 A1) discloses crystalline vortioxetine and various salts thereof. The US '240 A1, in addition, provides different polymorphic forms of vortioxetine hydrobromide—alpha, beta, gamma and hemihydrate forms and a mixture of ethyl acetate solvate and alpha form. The US '240 A1 also discloses seven alternative processes for preparation of vortioxetine. The US '240 A1 discloses that the compound 1,1-[2-(2,4-dimethylphenylsulfanyl)phenyl]piperazine as free base prepared in example 1(e) of WO 03/029232 A1 is in non-crystalline form.

U. S. PG-Pub. No. 2012/004409 A1 discloses a process for purification of vortioxetine hydrobromide salt and an isopropanol solvate thereof.

International (PCT) Publication No. WO 2013/102573 A1 also discloses a process for preparation of vortioxetine.

Crystalline solids normally require a significant amount of energy for dissolution due to their highly organized, lattice like structures. For example, the energy required for a drug molecule to escape from a crystal is more than from an amorphous or a non-crystalline form. It is known that the amorphous forms in a number of drugs exhibit different dissolution characteristics and in some cases different bioavailability patterns compared to the crystalline form (Econno T., *Chem. Pharm. Bull.,* 1990; 38: 2003-2007). For some therapeutic indications, one bioavailability pattern may be favored over another. An amorphous form of rosuvastatin calcium, rabeprazole sodium are some of the examples of one amorphous drug exhibiting much higher bioavailability than the crystalline forms, which leads to the selection of the amorphous form as the final drug substance for pharmaceutical dosage from development. Additionally, the aqueous solubility of crystalline atorvastatin calcium is lower than its amorphous form, which may result in the difference in their in vivo bioavailability. Therefore, it is desirable to have amorphous forms of drugs with high purity to meet the needs of regulatory agencies and also highly reproducible processes for their preparation.

In view of the above, it is therefore, desirable to provide an efficient, more economical, less hazardous and eco-friendly process for the preparation of amorphous vortioxetine or salts thereof and hydrates thereof. The amorphous form provided herein is at least stable under ordinary stability conditions with respect to purity, storage and is free flowing powder.

SUMMARY OF THE INVENTION

In one general aspect, there is provided amorphous vortioxetine hydrobromide of Formula (II).

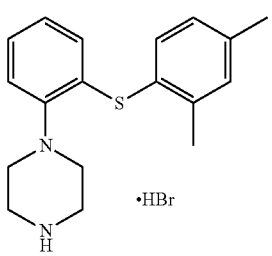

(II)

In another general aspect, there is provided a stable amorphous vortioxetine hydrobromide.

In another general aspect, there is provided the amorphous vortioxetine hydrobromide having water content from 0.5% to 5% wt/wt.

In another aspect, there is provided the amorphous vortioxetine hydrobromide having a purity by HPLC of greater than 98% and residual solvent less than 0.5%.

In another general aspect, there is provided a process for preparation of the amorphous vortioxetine hydrobromide, the process comprising:
(a) providing a solution of vortioxetine hydrobromide in one or more organic solvents; and
(b) obtaining the amorphous vortioxetine hydrobromide by the removal of the solvent.

In another general aspect, there is provided an amorphous solid dispersion of vortioxetine free base or salts thereof.

In another general aspect, there is provided a stable amorphous vortioxetine hydrobromide which is at least stable during storage and drying.

Figure 3:
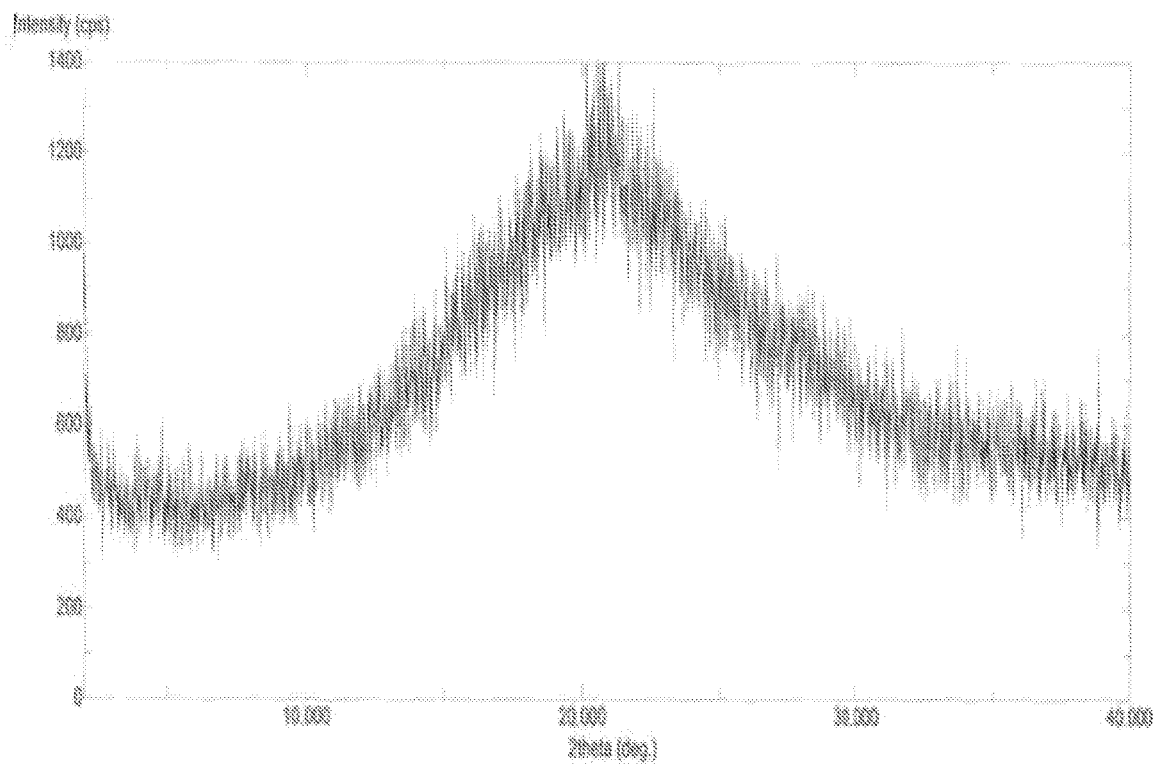

In another general aspect, there is provided an amorphous vortioxetine hydrobromide characterized by X-ray powder diffraction as depicted in FIG. 3.

In another general aspect, there is provided a pharmaceutical composition comprising amorphous vortioxetine hydrobromide together with one or more pharmaceutically acceptable carriers, excipients or diluents.

In another general aspect, there is provided a pharmaceutical composition comprising an amorphous vortioxetine solid dispersion and a polymer together with one or more of pharmaceutically acceptable carriers, excipients or diluents.

In another general aspect, there is provided an amorphous vortioxetine free base of Formula (I)

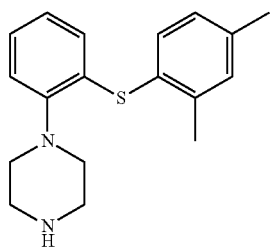

(I)

In another general aspect, there is provided the amorphous vortioxetine free base having water content from 0.5% to 5% wt/wt.

In another general aspect, there is provided a process for preparation of amorphous vortioxetine free base, the process comprising:
(a) providing a solution of vortioxetine in one or more organic solvents; and
(b) obtaining the amorphous vortioxetine free base by the removal of the solvent.

BRIEF DESCRIPTION OF THE FIGURES AND DRAWINGS

Figure 2:
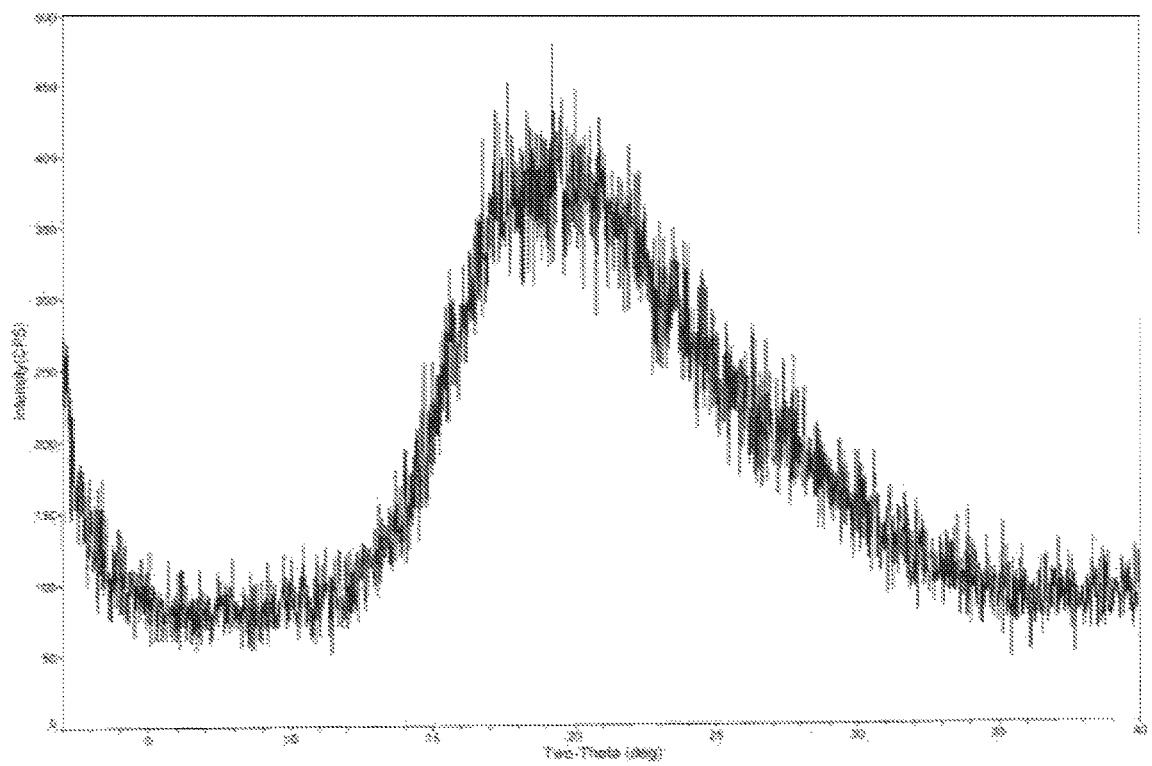

FIG. 1: X-ray diffractogram (XRD) of the amorphous vortioxetine hydrobromide as per example-2.
FIG. 2: X-ray diffractogram (XRD) of the amorphous vortioxetine hydrobromide as per example-4.
FIG. 3: X-ray diffractogram (XRD) of the amorphous vortioxetine hydrobromide as per example-5.

DETAILED DESCRIPTION OF THE INVENTION

The above and other objects of the present invention are achieved by the process of the present invention, which leads a process for the preparation of an amorphous vortioxetine free base or salts thereof.

Optionally, the solution, prior to any solids formation, can be filtered to remove any undissolved solids or solid impurities prior to removal of the solvent. Any filtration system and filtration techniques known in the art can be used.

All ranges recited herein include the endpoints, including those that recite a range "between" two values. Term "substantially" is to be construed as modifying a term or value such that it is not an absolute. This includes, at very least, the degree of expected experimental error, technique error and instrument error for a given technique used to measure a value.

As used herein, the term "stable" herein means amorphous vortioxetine hydrobromide that does not convert to any other solid form and contains less than 0.5% (wt/wt) total impurities when stored at a temperature of up to about 40° C. and at a relative humidity of about 25% to about 75% for about three months or more.

As used herein, the term "solid dispersion" means any solid composition having at least two components. In certain embodiments, a solid dispersion as disclosed herein includes an active ingredient vortioxetine hydrobromide dispersed among at least one other component, for example a polymer.

The term "immobilize" as used herein with reference to the immobilization of the active compound i.e. vortioxetine hydrobromide in the polymer matrix, means that molecules of the active compound interact with molecules of the polymer in such a way that the molecules of the vortioxetine are held in the aforementioned matrix and prevented from crystal nucleation due to lack of mobility.

In general, vortioxetine free base or vortioxetine hydrobromdie to be used as the starting material may be prepared by the known methods reported in the prior art i.e. for example by using the process as disclosed in U.S. Pat. No. 7,144,884 B2 which is incorporated herein as reference.

In one general aspect, there is provided amorphous vortioxetine hydrobromide of Formula (II).

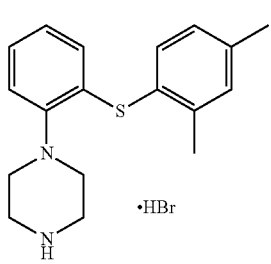

(II)

In another general aspect, there is provided amorphous vortioxetine hydrobromide having water content less than 0.5% wt/wt.

In another general aspect, there is provided amorphous vortioxetine hydrobromide having a purity by HPLC greater than 98% and residual solvents less than 0.5%.

In general, the amorphous vortioxetine hydrobromide is substantially free from residual solvents. The term "substantially free" means residual solvents within the permissible ICH limits suitable for pharmaceutical preparations. For example but not limited to less than 0.5%, particularly less than 0.3% or more particularly less than 0.2%.

In another general aspect, there is provided a process for preparation of amorphous vortioxetine hydrobromide, the process comprising:

(a) providing a solution of vortioxetine hydrobromide in one or more of organic solvents; and
(b) obtaining the amorphous vortioxetine hydrobromide by the removal of the solvent.

In general, a solution of vortioxetine hydrobromide in one or more organic solvents is obtained by the known methods that include:
(i) direct use of a reaction mixture containing vortioxetine free base that is obtained in the course of its synthesis; or
(ii) dissolving vortioxetine free base in one or more organic solvents.

In general, in step a) any physical form of vortioxetine hydrobromide may be utilized for providing the solution of vortioxetine hydrobromide in one or more organic solvents. The dissolution temperatures may be from 0° C. to the reflux temperature of the solvent. In particular, the dissolution may be performed from 25° C. to 120° C., more particularly, from about 40° C. to about 100° C. so as to obtain the clear solution of vortioxetine hydrobromide.

In general, the organic solvent of step a) comprises one or more of water, alcohols selected from methanol, ethanol, isopropanol (IPA), n-butanol, t-butanol, 1-butanol, 1-pentanol, 2-pentanol, amyl alcohol, ethylene glycol and glycerol; ketones selected from acetone, butanone, 2-pentanone, 3-pentanone, methylbutyl ketone, and methyl isobutyl ketone; esters selected from ethyl acetate, propyl acetate, isopropyl acetate, t-butyl acetate, and isobutyl acetate; halogenated hydrocarbons selected from methylene dichloride, ethylene dichloride, carbon tetrachloride and chlorobenzene; nitriles like acetonitrile; dioxane, dimethylsulfoxide (DMSO) or mixture thereof.

Step b) involves removal of the solvent to obtain an amorphous vortioxetine hydrobromide. The isolation may be affected by removing solvent. Techniques which may be used for the removal of solvent include distillation, distillation under vacuum, spray drying, agitated thin film dyring ("ATFD"), and freeze drying (lyophilization).

The solvent may be removed, optionally under reduced pressures, at temperatures less than 70° C., less than 60° C., less than 50° C.

In general, freeze drying (lyophilization) may be performed by freezing a solution of vortioxetien hydrobromide at low temperatures and reducing the pressure to remove the solvent from the frozen solution of vortioxetine hydrobromide. Temperatures that may be required to freeze the solution, depending on the solvent chosen to make the solution of vortioxetine hydrobromide may range from 70° C. to 10° C.

Alternatively, isolation can be effected by addition of one or more anti-solvent to the solution obtained in step a), optionally by concentrating the solution obtains in step a). An anti-solvent comprises one or more of hydrocarbons selected from hexanes, n-heptane, n-pentane, cyclohexane, and methylcyclohexane; aromatic hydrocarbons selected from toluene, xylene, chlorobenzene, and ethylbenzene; ethers selected from diethyl ether, diisopropyl ether, t-butyl methyl ether, dibutyl ether, tetrahydrofuran, and 2-methoxyethanol. In general, the preferred aspect of the invention involves spray drying of vortioxetine hydrobromide solution comprises of spray drying of feed stock, which is prepared as discussed below, wherein any solid forms of vortioxetine hydrobromide is used. In particular, the spray drying of vortioxetine hydrobromide may be performed maintaining the inlet temperature in the range of 35° C.-80° C., nitrogen pressure of 2-6 kg/cm$^2$, maintaining the outlet temperature in the range of 30° C. to 60° C., at a feed rate of 15% to 20% and maintaining the vacuum at 30-120 mm of Hg.

In further aspect, the feed stock of vortioxetine hydrobromide is conveniently prepared by dissolving any known solid forms or wet cake of vortioxetine hydrobromide in the solvent comprising one or more of water, methanol, ethanol, n-propanol, isopropanol (IPA), n-butanol, t-butanol, tetrahydrofuran, 1,4-dioxane, 2-methoxyethanol.

In general aspect, the amorphous vortioxetine hydrobromide obtained is formed into a finished dosage form.

In general, the finished dosage form comprises one or more of liquid, solid and semisolid dosage forms depending upon the route of administration. In particular, dosage forms are essentially pharmaceutical products in the form involving a mixture of amorphous vortioxetine hydrobromide together alongwith the pharmaceutically acceptable carriers, excipients or diluents.

As used herein, the term "pharmaceutical products" includes pharmaceutical formulations selected from tablets, pills, powders, liquids, suspensions, emulsions, granules, capsules, suppositories, or injection preparations.

In one general aspect, there is provided a composition comprising an amorphous vortioxetine free base or amorphous vortioxetine hydrobromide. In particular, the composition is a solid dispersion that includes amorphous vortioxetine free base or amorphous vortioxetine hydrobromide and a polymer.

In another general aspect, there is provided an amorphous solid dispersion of vortioxetine free base or salts thereof and a polymer.

In general, the polymer may be a non-ionic polymer or an ionic polymer. The polymer comprises of hydroxypropylmethyl cellulose acetate succinate (HPMC-AS), hydroxypropylmethyl cellulose (HPMC), methacrylic acid copolymers and polyvinyl pyrrolidone (PVP). In particular, PVP of different grades like K-15, K-30, K-60, K-90 and K-120 may be used for the preparation of amorphous composition. More particular, hydroxypropylmethyl cellulose (HPMC) or its acetate succinate and PVP K-30 may be used. HPMC with viscosity 8 cps, 5 cps or 3 cps may be used.

In general, the salts comprises of pharmaceutically acceptable salts of vortioxetine selected from hydrochloride, hydrobromide, hydrogen sulfate, phosphate, nitrate, acetate, ascorbate, benzoate, besylate, mesylate, succinate, oxalate, citrate, formate, fumarate, lactate, malonate, maleate, malate, palmitate, tartrate, and triflouroacetate.

In general, the vortioxetine free base or its hydrobromide salt are mixed with a polymer optionally in the presence of one or more organic solvents.

In another general aspect there is provided a process for the preparation of an amorphous solid dispersion of vortioxetine or salts thereof, the process comprising;
(a) mixing vortioxetine free base or salts thereof with a polymer; and
(b) obtaining solid dispersion of vortioxetine free base or salts thereof.

In general, the amorphous solid dispersion of vortioxetine free base or its hydrobromide salt can be obtained optionally by removal of one or more organic solvents.

The organic solvent comprises one or more of low boiling solvents selected from methanol, ethanol, isopropanol, acetone and ethyl acetate.

In some aspects, the vortioxetine free base or vortioxetine hydrobromide may be dispersed within a matrix formed by a polymer in its solid state such that it is immobilized in its amorphous form. The polymer may prevent intramolecular hydrogen bonding or weak dispersion forces between two or more drug molecules of vortioxetine free base or vortioxetine hydrobromide. The solid dispersion provides for a large surface area, thus further allowing for improved dissolution and bioavailability of vortioxetine free base or vortioxetine hydrobromide.

In some aspects, the ratio of the amount of weight of vortioxetine free base of Formula (I) or vortioxetine hydrobromide of Formula (II) within the solid dispersion to the amount by weight of the polymer therein is from 1:1 to 1:10. The composition of vortioxetine free base of Formula (I) or vortioxetine hydrobromide with polymer selected from PVP K-30, HPMC or HPMC-AC may be prepared by using 1:1 to 1:10 polymers with respect to vortioxetine free base of Formula (I) or vortioxetine hydrobromide of Formula (II). The usage of higher molar amount of polymer increases the amorphous character of the drug substance.

In another general aspect there is provide a process for the preparation of composition of amorphous vortioxetine free base of Formula (I) or vortioxetine hydrobromide of Formula (II) having at least one polymer, the process comprises mixing vortioxetine free base of Formula (I) or vortioxetine hydrobromide of Formula (II) with a polymer in one or more organic solvents and obtaining amorphous composition of vortioxetine free base of Formula (I) or vortioxetine hydrobromide of Formula (II) by removal of the solvent.

The compound vortioxetine free base of Formula (I) or vortioxetine hydrobromide of Formula (II) and a polymer (for example HPMC or PVP K-30) may be dissolved in one or more organic solvents having a low boiling point selected from methanol, ethanol, isopropanol, acetone or ethyl acetate. The amorphous solid dispersion may be obtained by removal of solvent (for example by spray drying, lyophilization, flash evaporation, vacuum distillation) thereby leaving the amorphous solid dispersion precipitated in a matrix formed by the polymer.

In general, there is provided an amorphous solid dispersion of vortioxetine hydrobromide susbtantially free from crystalline forms and residual solvents.

In another general aspect, there is provided an amorphous solid dispersion of vortioxtine hydrobromide having purity by HPLC of more than 98%.

In another general aspect, there is provided an amorphous vortioxetine free base of Formula (I).

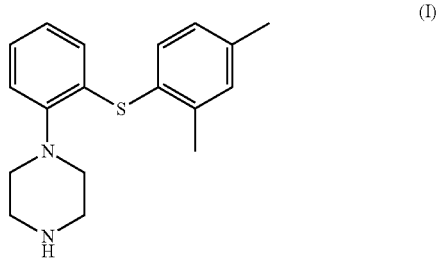 [SMILES: Cc1ccc(Sc2ccccc2N2CCNCC2)c(C)c1]

In another general aspect, there is provided an amorphous vortioxetine free base having purity by HPLC greater than 99% and residual solvents less than 0.5%.

In another general aspect, there is provided a process for preparation of amorphous vortioxetine free base, the process comprising:
(a) providing a solution of vortioxetine free base in one or more organic solvent; and
(b) obtaining the stable amorphous form of vortioxetine free base by the removal of the solvent.

In general, a solution of vortioxetine free base in one or more organic solvents is obtained by the known methods that include:

(i) direct use of a reaction mixture containing vortioxetine free base that is obtained in the course of its synthesis; or
(ii) dissolving vortioxetine free base in one or more organic solvents.

In general, in step a) any physical form of vortioxetine free base may be utilized for providing the solution of vortioxetine free base in one or more organic solvents. The dissolution temperatures may be from 0° C. to the reflux temperature of the solvent. In particular, the dissolution may be performed from 25° C. to 120° C., more particularly, from about 40° C. to about 100° C. so as to obtain the clear solution of vortioxetine free base.

In general, the organic solvent of step a) comprises one or more of alcohols selected from methanol, ethanol, isopropanol (IPA), n-butanol, t-butanol, 1-butanol, 1-pentanol, 2-pentanol, amyl alcohol, ethylene glycol and glycerol; ketones selected from acetone, butanone, 2-pentanone, 3-pentanone, methylbutyl ketone, and methyl isobutyl ketone; esters selected from ethyl acetate, propyl acetate, isopropyl acetate, t-butyl acetate, and isobutyl acetate; hydrocarbons selected from toluene, mix-xylene, m-xylene, o-xylene, p-xylene, pentane, hexane, n-heptane, octane and cyclohexane; halogenated hydrocarbons selected from methylene dichloride, ethylene dichloride, carbon tetrachloride and chlorobenzene; nitriles like acetonitrile; dioxane, dimethylsulfoxide (DMSO) or mixture thereof. More particularly, acetone, toluene, ethyl acetate or methylene dichloride may be used.

Step b) involves removal of the solvent to obtain an amorphous vortioxetine free base. The isolation may be affected by removing solvent. Techniques which may be used for the removal of solvent include distillation, distillation under vacuum, spray drying, agitated thin film dyring ("ATFD"), and freeze drying (lyophilization).

The solvent may be removed, optionally under reduced pressures, at temperatures less than 80° C., less than 70° C., less than 60° C., less than 50° C., less than 40° C. or less 30° C.

In general, freeze drying (lyophilization) may be performed by freezing a solution of vortioxetine free base at low temperatures and reducing the pressure to remove the solvent from the frozen solution of vortioxetine free base. Temperatures that may be required to freeze the solution, depending on the solvent chosen to make the solution of vortioxetine free base may range from 70° C. to 10° C.

Alternatively, isolation can be effected by addition of one or more of anti-solvent to the solution obtain in step a), optionally by concentrating the solution obtained in step a). Anti-solvents that may be used comprises of one which reduces the solubility of vortioxetine in the solution, causing the crystallization or precipitation spontaneously or upon stirring. In particular, the suitable anti-solvent may be added to the solution of vortioxetine or vortioxetine solution may be added to the suitable anti-solvent.

In general, anti-solvent comprises one or more of water, diethylether, diisopropyl ether, methyl tert-butyl ether, 1,4-dioxane and 2-methoxyethanol.

In one preferred aspect, there is provided process for spray drying a solution of vortioxetine free base that involves spray drying of feed stock, which may be prepared conveniently by dissolving any known forms or wet cake of vortioxetine free base in one or more of organic solvents selected from methanol, ethanol, isopropanol (IPA), n-butanol, acetone, ethyl acetate, isopropyl acetate, isobutyl acetate, methylene dichloride, acetonitrile, and tetrahydrofuran. More particularly, methanol, acetone, ethyl acetate or methylene dichloride may be used.

In another preferred feature, the spray drying of vortioxetine free base may be performed maintaining the inlet temperature in the range of 35° C. to 80° C., nitrogen pressure of 2 to 6 kg/cm$^2$, maintaining the outlet temperature in the range of 30° C. to 60° C., at a feed rate of 15% to 20% and maintaining the vacuum at 30 to 120 mm of Hg.

Any known form of vortioxetine free base or the filtered cake that is obtained as an end result of the reaction or reaction mass comprising vortioxetine free base or solution comprising vortioxetine free base may be used for the preparation of feed stock.

The obtained amorphous vortioxetine free base is stable under normal stability conditions and substantially free from residual solvent. Therefore, there is no physical change observed from amorphous form to crystalline form during the stability.

In further aspect, the stable amorphous vortioxetine free base or vortioxetine hydrobromide can be stored under nitrogen atmosphere and packed in a double polythene bag tied with a thread, keeping primary packing containing amorphous vortioxetine or vortioxetine hydrobromide inside a black color polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at 25° C. and/or 40° C.

In another general aspect, the present invention provides an amorphous vortioxetine hydrobromide having purity by HPLC of >98%. In particular, the purity by HPLC of >99%, more particularly, the purity by HPLC of >99.5%, further more particularly, the purity by HPLC of >99.8%, most particularly, the purity by HPLC>99.9%.

In another general aspect, there is provided amorphous vortioxetine hydrobromide having particle size distributions wherein the 10th volume percentile particle size D(10) of about 50 μm or less; the 50th volume percentile particle size D(50) of about 200 μm or less; or the 90th volume percentile particle size D(90) of about 400 μm or less. In particular, particle size distribution wherein D(10) of about 25 μm or less; D(50) of about 100 μm or less; D(90) of about 250 μm or less.

In another general aspect there is provided a pharmaceutical composition comprising an amorphous vortioxetine hydrobromide having particle size D(10) of about 50 μm or less, D(50) of about 200 μm or less, D(90) of about 400 μm or less together with one or more of pharmaceutically acceptable carriers, excipients or diluents.

Powder X-ray Diffraction of amorphous vortioxetine free base or vortioxetine hydrobromide can be obtained under following conditions.

(i) Characterization by Powder X-Ray Diffraction

Analytical method: Powder X-ray Diffractioncan be performed using a Rigaku D/MAX 2200 VPC diffraction meter or PANALYTICAL ExpertPro DY2408 or other suitable machines in practice, the powder X-ray diffraction pattern was measured at room temperature using a Cu Kα filled tube (40 kV, 40 mA) as the X-ray source with a wide-angle goniometer, a 1° scattering slit, an 1° diverging slit, a graphite secondary monochromator and a scintillation counter. Data collection was done in 2θ continuous scan mode at a scan speed of 3°/minute in scan steps of 0.02° in the range of 2° to 40°.

In another general aspect, there is provided a pharmaceutical compositions comprising an amorphous vortioxetine hydrobromide together with pharmaceutical acceptable carriers, excipients or diluents.

In another general aspect, there is provided a pharmaceutical composition comprising an amorphous solid dispersion of vortioxetine hydrobromide and a polymer together with one or more pharmaceutically acceptable carriers, excipients or diluents.

In another general aspect, there is provided a pharmaceutical composition comprising a stabilized amorphous solid dispersion of vortioxetine hydrobromide and a polymer together with one or more pharmaceutically acceptable carriers, excipients or diluents.

In general, the pharmaceutical compositions containing the vortioxetine free base of Formula I or vortioxetine hydrobromide of Formula II may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

While the present invention has been described in terms of its specific embodiments, certain modifications and equivalents will be apparent to those skilled in the art and are intended to be included within the scope of the present invention.

EXAMPLES

Example-1: Preparation of Amorphous Vortioxetine (I)

In 250 mL three necked round bottom flask equipped with mechanical stirrer, thermometer and an addition funnel, 25 g of vortioxetine was dissolved in 250 mL of methanol at 25° C. to 30° C. The content was stirred for 30 minutes at 25° C. to 30° C. To this, 1.0 g charcoal was added and stirred for 30 minutes at 60° C. The content was filtered through Hyflosupercel, and the Hyflosupercel pad washed with 50 mL methanol. The filtrate was concentrated under vacuum below 45° C. till 100 mL methanol remains. 50 mL methanol was added and stirred at 60° C. to get clear solution followed by spray drying in JISL Mini spray drier LSD-48 by maintaining the inlet temperature in the range of 70° C. under nitrogen pressure of 5 kg/cm$^2$ at a feed rate of 20% and maintaining the outlet temperature in the range of 50° C. The product was collected from cyclone and was further dried at 40° C.±5° C. under vacuum for 12 hours to get 17 g of amorphous vortioxetine.

Example-2: Preparation of Amorphous Vortioxetine Hydrobromide (II)

In 250 mL three necked round bottom flask equipped with mechanical stirrer, thermometer and an addition funnel, 25.0 g of vortioxetine hydrobromide was dissolved in 250 mL of water at 25° C. to 30° C. The content was stirred for 30 minutes at 25° C. to 30° C. To this, 1.0 g charcoal was added and stirred for 30 minutes at 80° C. The content was filtered through Hyflosupercel, and the Hyflosupercel pad washed with 50 mL water. The filtrate was heated at 80° C. to get clear solution followed by spray drying in JISL Mini spray drier LSD-48 by maintaining the inlet temperature in the range of 60° C. under nitrogen pressure of kg/cm$^2$ at a feed rate of 15% and maintaining the outlet temperature in the range of 50° C. The product was collected from cyclone and was further dried at 40° C.±5° C. under vacuum for 12 hours to get 15 g of amorphous vortioxetine. The obtained solid was amorphous as is shown by the X-ray diffraction pattern given in FIG. 1.

Example-3: Preparation of Amorphous Solid Dispersion of Vortioxetine (I)

In 250 mL three necked round bottom flask equipped with mechanical stirrer, thermometer and an addition funnel, 10 g of vortioxetine and 150 mL methanol were taken in round bottom flask at 25-30° C. The reaction mixture was heated at 45-50° C. to obtain clear solution. 10 g of PVP-K30 polymer was added and stirred at 45-50° C. for 2 hours. The reaction mixture was distilled under vacuum at 60-65° C. The product was dried under vacuum at 55-60° C. to obtain 7 g amorphous vortioxetine.

Example-4: Preparation of Amorphous Solid Dispersion of Vortioxetine Hydrobromide (II)

In 250 mL three necked round bottom flask equipped with mechanical stirrer, thermometer and an addition funnel, 10 g of vortioxetine hydrobromide and 150 mL water were taken at 25-30° C. The reaction mixture was heated at 60-70° C. to obtain clear solution. 10 g of PVP-K30 polymer was added and stirred at 60-70° C. for 2 hours. The reaction mixture was distilled under vacuum at 60-65° C. The product was dried under vacuum at 55-60° C. to obtain 7 g amorphous vortioxetine hydrobromide. The obtained solid was amorphous as is shown by the X-ray diffraction pattern given in FIG. 2.

Example-5: Preparation of Amorphous Solid Dispersion of Vortioxetine Hydrobromide (II)

In 50 mL three necked round bottom flask equipped with mechanical stirrer, thermometer and an addition funnel, 1 g of vortioxetine hydrobromide and 20 mL methanol were taken at 25-30° C. The reaction mixture was heated at 50-55° C. to obtain clear solution. 1 g of HPMC (3 cps) polymer was added and stirred at 50-55° C. for 15 minutes. The reaction mixture was distilled under vacuum at 60-65° C. The product was dried under vacuum at 55-60° C. to obtain 1.7 g amorphous solid dispersion of vortioxetine hydrobromide. The obtained solid was amorphous as is shown by the X-ray diffraction pattern given in FIG. 3.

While the present invention has been described in terms of its specific embodiments, certain modification and equivalents will be apparent to those skilled in art and the intended to be included within the scope of the invention.

We claim:

1. Amorphous vortioxetine hydrobromide of Formula (II) having a purity by HPLC of greater than 98%,

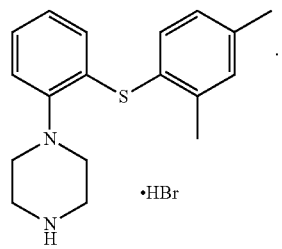

(II)

2. A stable amorphous vortioxetine hydrobromide that does not convert to any other solid form and contains less than 0.5% (wt/wt) total impurities when stored at a temperature of up to about 40° C. and at a relative humidity of about 25% to about 75% for about three months.

3. The amorphous vortioxetine hydrobromide according to claim 1 having a residual solvent less than 0.5%.

4. A solid dispersion of amorphous vortioxetine free base or salts thereof having a purity by HPLC of more than 98% and a polymer.

5. The solid dispersion according to claim 4, wherein the polymer is a non-ionic polymer or an ionic polymer.

6. The solid dispersion according to claim 5, wherein the polymer comprises one or more of hydroxypropylmethyl cellulose acetate succinate, hydroxypropylmethyl cellulose, methacrylic acid copolymers, and polyvinyl pyrrolidone.

7. The solid dispersion according to claim 4, wherein the salt is a hydrobromide salt.

8. The solid dispersion according to claim 4 substantially free from residual solvents.

9. A pharmaceutical composition comprising amorphous vortioxetine hydrobromide having purity by HPLC of more than 98% together with one or more pharmaceutically acceptable carriers, excipients or diluents.

10. A pharmaceutical composition comprising a solid dispersion of amorphous vortioxetine hydrobromide having purity by HPLC of more than 98% and a polymer together with one or more of pharmaceutically acceptable carriers, excipients or diluents.

11. The amorphous vortioxetine hydrobromide according to claim 1, having particle size distributions,
   D(10) of about 50 µm or less, D(50) of about 200 µm or less, and D(90) of about 400 µm or less; or
   D(10) of about 25 µm or less, D(50) of about 100 µm or less and D(90) of about 250 µm or less.

12. A pharmaceutical composition comprising the amorphous vortioxetine hydrobromide according to claim 1, having particle size distributions,
   D(10) of about 50 µm or less, D(50) of about 200 µm or less and D(90) of about 400 µm or less; or
   D(10) of about 25 µm or less, D(50) of about 100 µm or less and D(90) of about 250 µm or less together with one or more of pharmaceutically acceptable carriers, excipients or diluents.

13. The amorphous vortioxetine hydrobromide according to claim 1, having particle size distribution, D(10) of about 50 µm or less, D(50) of about 200 µm or less and D(90) of about 400 µm or less.

* * * * *